US00PP36864P2

(12) United States Plant Patent
Nir

(10) Patent No.: US PP36,864 P2
(45) Date of Patent: Jul. 29, 2025

(54) ***CHAMELAUCIUM* PLANT NAMED 'GRAND ADI'**

(50) Latin Name: *Chamelaucium uncinatum*
Varietal Denomination: GRAND ADI

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 0 days.

(21) Appl. No.: 18/889,489

(22) Filed: Sep. 19, 2024

(51) Int. Cl.
*A01H 5/02* (2018.01)
*A01H 6/00* (2018.01)

(52) U.S. Cl.
USPC ..... Plt./229

(58) Field of Classification Search
USPC ..... Plt./226, 229
See application file for complete search history.

(56) References Cited

U.S. PATENT DOCUMENTS

PP28,274 P2 * 8/2017 Nir ..... A01H 6/00 Plt./229
PP35,095 P2 * 4/2023 Nir ..... Plt./229

* cited by examiner

*Primary Examiner* — Karen M Redden
(74) *Attorney, Agent, or Firm* — Cassandra Bright

(57) ABSTRACT

A new and distinct cultivar of *Chamelaucium* plant named 'GRAND ADI' is disclosed, characterized by plants producing large purple flowers in winter. Flower buds and round and uniquely brown and purple. The new variety is a *Chamelaucium*, normally producing cut flower stems, or as a garden or container plant.

1 Drawing Sheet

Latin name of the genus and species: *Chamelaucium uncinatum.*

Variety denomination: 'GRAND ADI'.

BACKGROUND OF THE INVENTION

The new *Chamelaucium* cultivar is the product of a planned breeding program conducted by the inventor, Nitzan Nir, in Kfar Hess, Israel. The objective of the breeding program was to produce new *Chamelaucium* varieties for ornamental commercial applications. The new variety was selected as a seedling from the breeding program at a commercial nursery in Kfar Hess, Israel.

The crossing resulting in this new variety was made in January of 2017. The seed parent is the unpatented variety referred to as *Chamelaucium uncinatum* 'Guy'. The pollen parent is the unpatented variety referred to as *Chamelaucium uncinatum* 'Atar L'. The new variety was discovered in February 2018 by the inventor in a group of seedlings resulting from previously mentioned crossing, in a commercial nursery in Kfar Hess, Israel.

Asexual reproduction of the new cultivar has been performed by terminal vegetative cuttings. This was first performed in May of 2020 at a commercial nursery in Kfar Hess, Israel and has shown that the unique features of this cultivar are stable and reproduced true to type in at least 5 successive generations.

SUMMARY OF THE INVENTION

The cultivar 'GRAND ADI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GRAND ADI'. These characteristics in combination distinguish 'GRAND ADI' as a new and distinct *Chamelaucium* cultivar:

1. Large purple flowers.
2. Brown upper receptacle color.
3. Winter blooming.
4. Round bud shape.
5. Large purple-brown buds.

PARENT COMPARISONS

Plants of the new cultivar 'GRAND ADI' are similar to plants of the seed parent in most horticultural characteristics, however, plants of the new cultivar 'GRAND ADI' differ in the following:

1. Flower size of the new variety is larger than the flower size of the seed parent.
2. Flower color of the new variety is purple, while the flower color of the seed parent is white.
3. Upper receptacle color of the new variety is brown, while the upper receptacle color of the seed parent is green when opening, then turns brown.

Plants of the new cultivar 'GRAND ADI' are similar to plants of the pollen parent in most horticultural characteristics, however, plants of the new cultivar 'GRAND ADI' differ in the following:

1. Flower size of the new variety is larger than the flower size of the pollen parent.
2. Flower color of the new variety is purple, while the flower color of the pollen parent is white.
3. Bud color of the new variety is purple-brown, while the bud color of the pollen parent is green.

4. Buds of the new variety are larger than buds of the pollen parent.

COMMERCIAL COMPARISONS

Plants of the new cultivar 'GRAND ADI' are similar to plants of the unpatented commercial variety *Chamelaucium* 'Adi' in most horticultural characteristics; however, plants of the new cultivar 'GRAND ADI' differ in the following:

1. Flowers of the new variety bloom later than flowers of this comparator.
2. Flower size of the new variety is larger than the flower size of this comparator.
3. Upper receptacle color of the new variety is brown, while the upper receptacle color of this comparator is yellow-green when opening, then turns brown.

Plants of the new cultivar 'GRAND ADI' are similar to plants of the unpatented commercial variety *Chamelaucium* 'Purple Pride' in most horticultural characteristics; however, plants of the new cultivar 'GRAND ADI' differ in the following:

1. Flower size of the new variety is larger than the flower size of this comparator.
2. Buds of the new variety are larger than buds of this comparator.

Plants of the new cultivar 'GRAND ADI' are similar to plants of the commercial variety *Chamelaucium* 'Sirius' U.S. Plant Pat. No. 35,299 in most horticultural characteristics; however, plants of the new cultivar 'GRAND ADI' differ in the following:

1. Flower size of the new variety is larger than the flower size of this comparator.
2. Flower color of the new variety is purple; flower color of this comparator is white.

BRIEF DESCRIPTION OF THE PHOTOGRAPH

The accompanying photograph illustrates in full color a close up of typical flowers and foliage of 'GRAND ADI' on a mature stem at approximately 1 year of age. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'GRAND ADI' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum* 'GRAND ADI'.

PROPAGATION

Time to produce a rooted plantlet: 30 to 60 days at approximately 24° C.

Root description: Split root.

PLANT

Age of plant described: About 2 months old from a rooted cutting.

Height: 130 cm to top of foliage; 127 cm to top of flowers.

Plant spread: 120 cm.

Branching characteristics:

Quantity of primary lateral branches: 100 to 120.

Characteristics of primary lateral branches:

*Length.*—60 to 120 cm.

*Diameter.*—0.5 cm, measured at 50 cm from top.

*Color.*—Near RHS Greyed-Orange 177C and 177D.

*Texture.*—Smooth.

*Strength.*—Medium.

Internode length: 2 to 9 cm (section of top 30 cm).

FOLIAGE

Leaf:

*Arrangement.*—Opposite.

*Quantity.*—Approximately 10 leaves in the 5-10 cm section from the top of the branch.

*Length.*—1.4 cm.

*Width.*—1 mm.

*Shape.*—Needle.

*Apex.*—Acute.

*Base.*—Truncate.

*Margin.*—Entire.

*Texture.*—Smooth both surfaces.

*Aspect.*—Straight, occurring at about 15 degrees from stem.

*Color.*—Young foliage, upper side: RHS Green 137C. Young foliage, under side: RHS Green 137C. Mature foliage, upper side: RHS Green 137A. Mature foliage, under side: RHS Green 137A.

*Venation.*—Indistinguishable from foliage.

*Petiole.*—Not present.

FLOWER

Natural flowering season: Winter.

Days to flowering from rooted cutting: Photoperiodic conditions. No juvenility.

Typical flowering stems harvested per plant: 100 to 120 during the course of the season.

Vase life of flowers: Two weeks.

Individual flower type: 5 petals, about 2.3 cm in diameter.

Rate of flower opening: About 40 to 60 days from bud to fully opened flower.

Persistence: Self-cleaning.

Bud:

*Shape.*—Round.

*Length.*—0.7 cm.

*Diameter.*—0.5 cm.

*Color.*—RHS Greyed-Red 179A flushed Red-Purple 70B and 70C.

Flower size:

*Diameter.*—2.3 cm.

*Length.*—1.1 cm.

Corolla:

Petals:

*Arrangement*.—Rotate

*Length*.—0.77 cm.

*Diameter*.—0.75 cm.

*Quantity*.—5.

*Texture*.—Smooth both surfaces.

*Apex*.—Rounded, with infrequent very shallow crenations.

*Base*.—Fused.

*Color*.—When opening: Upper surface: RHS Red-Purple N74C. Lower surface: RHS White N155B. Fully opened: Upper surface: RHS Red-Purple 72B. Lower surface: RHS White N155B. Aging: Upper surface: RHS Red-Purple 72B. Lower surface: RHS Red-Purple 72B.

Interior corolla/tube:

*Diameter*.—0.8 cm.

*Length*.—0.35 cm.

*Color*.—When opening: Upper surface: RHS Green-Yellow 152B. Lower surface: RHS Greyed-Orange 166C. Fully opened: Upper surface: RHS Grey-Brown 199A. Lower surface: RHS Greyed-Orange 172A. Aging: Upper surface: RHS Greyed-Purple 187A. Lower surface: RHS Greyed-Purple 187A.

Calyx/sepals:

*Quantity per flower*.—5.

*Shape*.—Bow.

*Length*.—0.16 cm.

*Width*.—0.43 cm.

*Margin*.—Smooth.

*Texture*.—Smooth both surfaces.

*Color*.—RHS Purple-Red 72B.

Peduncle: Peduncle consists of the plant stem.

Pedicel:

*Length*.—1.6 to 2 cm.

*Diameter*.—0.09 to 0.11 cm.

*Color*.—RHS Yellow-Green 144A.

Fragrance: None.

REPRODUCTIVE ORGANS

Stamens:

*Number*.—10.

*Filament length*.—2 mm.

*Filament color*.—Near RHS Red 56D.

Anthers:

*Shape*.—Oval.

*Length*.—1 mm.

*Color*.—RHS Greyed-Yellow 160B.

*Pollen*.—Not observed.

Pistil:

*Number*.—1.

*Length*.—0.75 cm.

*Style length*.—0.7 cm.

*Style color*.—RHS White N155B.

*Stigma*.—Shape: Round. Color: RHS Greyed-Purple 187A.

OTHER CHARACTERISTICS

Seeds and fruits: Single flower produces one fruit. When the fruit is fertile, it will produce one seed. Fruit and seeds are too small for accurate measurement of characteristics.

Disease/pest resistance: Neither resistance nor susceptibility to the normal diseases and pests of *Chamelaucium* have been observed to date.

Temperature tolerance: From −2° C. to 35° C.

What is claimed is:

1. A new and distinct cultivar of *Chamelaucium* plant named 'GRAND ADI' as herein illustrated and described.

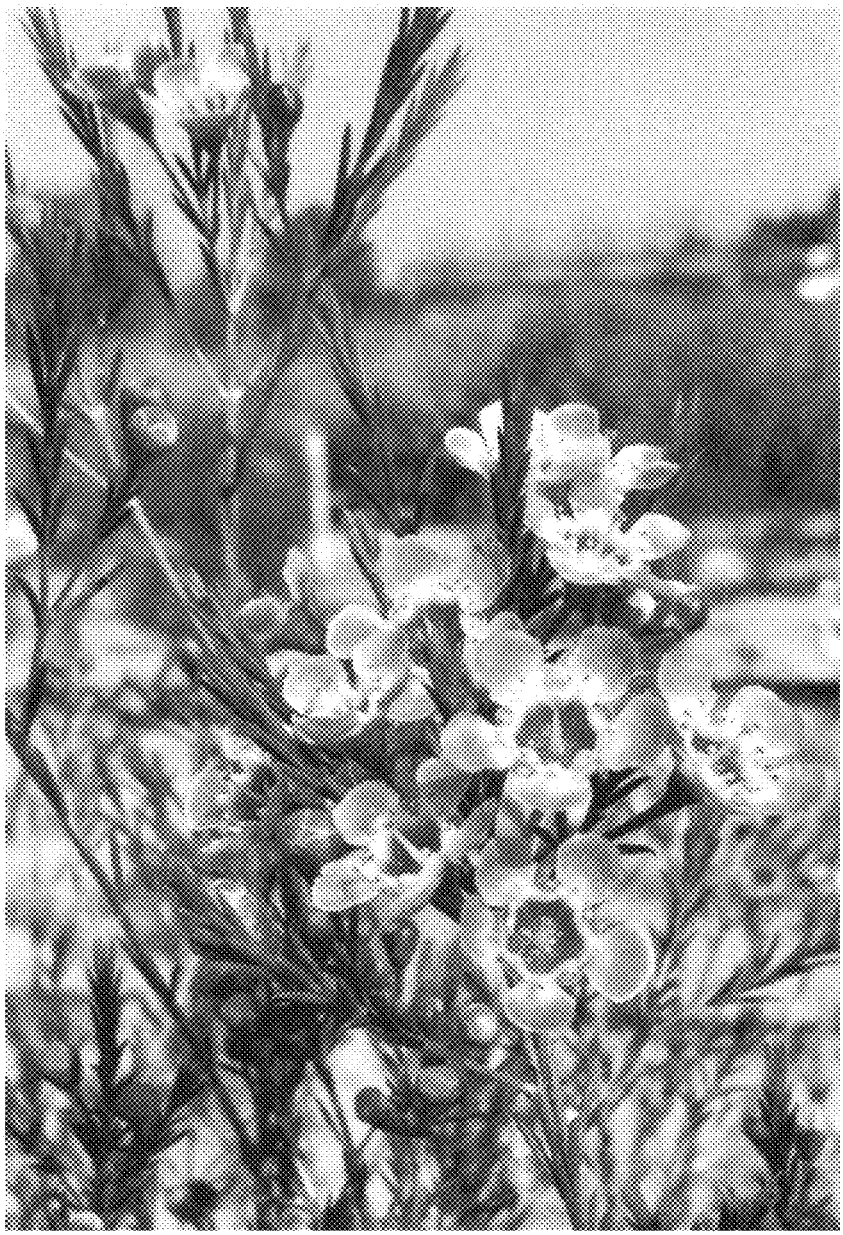

* * * * *